United States Patent [19]

Bracha et al.

[11] Patent Number: 4,854,965

[45] Date of Patent: Aug. 8, 1989

[54] HERBICIDAL COMPOSITIONS

[75] Inventors: Peretz Bracha, Omer; Moshe Korat, Beer-Sheva, both of Israel

[73] Assignee: Makhteshim Chemical Works, Ltd., Beer-Sheva, Israel

[21] Appl. No.: 67,418

[22] Filed: Jun. 22, 1987

[30] Foreign Application Priority Data

Jun. 26, 1986 [IL] Israel .......................................... 79249

[51] Int. Cl.$^4$ ............................................. A01N 43/52
[52] U.S. Cl. ........................................ 71/92; 544/285
[58] Field of Search ............................. 71/92; 544/285

[56] References Cited

U.S. PATENT DOCUMENTS 4,551,458 11/1985 Bracha et al. ....................... 544/285
4,605,657 8/1986 Edwards ............................. 544/285

Primary Examiner—Glennon H. Hollrah
Assistant Examiner—Amelia A. Owens
Attorney, Agent, or Firm—Browdy and Neimark

[57] ABSTRACT

Herbicidal compositions containing 2,4-dioxo-and 2,4-dithio-1,3-dihydroquinazolines and a method of controlling broadleaved weeds in cereals applying to said weeds a herbicidally effective amount of a composition containing said dihydroquinazolines.

8 Claims, No Drawings

HERBICIDAL COMPOSITIONS

BACKGROUND OF THE INVENTION

The present invention concerns new compositions and a method of using these compositions in treating weeds in a variety of crops. More specifically the present invention concerns new herbicidal compositions containing 2,4-dioxo- and 2,4-dithio-1,3-dihydroquinazolines, the use of these compounds in controlling weeds and especially against broadleaved weeds in cereals.

STATE OF PRIOR ART 2,4-Dioxo-1,3-dihydroquinazolines and their derivatives are known to possess microbicidal and herbicidal activity. For example, Skinner and Zell (J. Am. Chem. Soc., 77(1955)544) report the synthesis of some 2,4-quinazolinediones and their use as microbicides. U.S. Pat. No. 3,544,575 disclosed the preparation of a series of 2,4-quinazolinediones and their use as herbicides. The pesticidal activity of a variety of 2,4-quinazolinediones was described in U.S. Pat. Nos. 3,681,352; 3,706,748; and 3,781,288. 2-Thiono-4-oxo-1,3-dihydroquinazolines are also known and have been reported by Kappe, et. al |Monatsh. Chem., 98 (1967) 214(C.A., 66: 104980y)|. Certain compounds containing the >NSCCl3 group, as described in U.S. Pat. No. 2,553,770, are also known to be excellent fungicides. Recently, U.S. Pat. No. 4,551,458 disclosed the preparation of haloalkylthio-1,3-dihydro-2,4-dioxoquinazolines and their use as fungicides.

SUMMARY OF THE INVENTION

We have surprisingly found that haloalkylthio 1- and 3-substituted 2,4-dioxo and 2-thiono-4-oxo,1,3-dihydroquinazolines have herbicidal activity, particularly against broadleaved weeds in cereals. The haloalkylthio 1- and 3-substituted 2,4-dioxo and 2-thiono-4-oxo-1,3-dihydroquinazolines can be represented by the following formula:

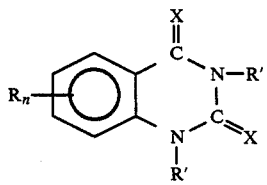

wherein
R is a hydrogen, a lower alkyl, cycloalkyl, lower alkoxy, amino, substituted amino, halogen, or nitro;
R' is selected from the group consisting of a haloalkylthio group containing 1 or 2 carbon atoms and at least two halogen substitutents: linear or branched alkyl and alkenyl group having from 2 to 10 carbon atoms, optionally substituted by halogen, hydroxy, lower alkoxy or haloalkyl; and cycloalkyl of 5 to 10 carbon atoms, optionally substituted by halogen, hydroxy, lower alkoxy, or halalkyl; provided that at least one of R' is a haloalkylthio group as defined;
n is zero or an integer from 1 to 4; and
X is oxygen or sulfur.

Examples of R falling within scope of the present invention are hydrogen, methyl, ethyl, propyl, butyl, and the isomeric form of these; methoxy, ethoxy, amino, dimethylamino, diethylamino, cyclopropyl, cyclobutyl, cyclopentyl, and cyclohexyl; and chlorine or bromine, with hydrogen and methyl being preferred.

Examples of R' falling within the scope of the present invention are propyl, butyl, pentyl, hexyl, octyl, and the isomeric form of these; cyclopropyl, cyclobutyl, cyclopentyl, and cyclohexyl, with n-propyl, iso-propyl, n-butyl, and cyclohexyl being preferred.

Examples of haloalkylthio groups of 1 or 2 carbon atoms (R') falling within the scope of the present invention are bromochlorofluoromethylthio, bromodichloromethylthio, chlorodifluoromethylthio, dichloromethylthio, fluorodichloromethylthio, 1-fluoro-1,1,2,2-tetrachloroethylthio, 1,1,2,2-tetrachloroethylthio, 2,2,2-trichloroethylthio, 1,2,2-trichloroethylthio, trichloromethylthio, and the like. The preferred group is one containing at least three chlorine atoms; and most preferred is the trichloromethylthio group.

The present invention requires that at least one and possibly both R' groups be haloalkylthio as defined above. A preferred embodiment is when one R' is a haloalkylthio group, and one R' is an alkyl or cycloalkyl group as defined; and most preferred when one R' is n-propyl, iso-propyl, n-butyl, or cyclohexyl and X is oxygen.

The compounds of the present invention were found to exhibit both pre- and post-emergence herbicidal activity. Said activity was especially found in broadleaved weeds in cereals and most preferably against broadleaved weeds in oats. Such selectivity was especially found in compounds where R=H or CH3, one R'=trihalomethylthio (as SCCl3), and the other R'=n-propyl, iso-propyl, n-butyl, cyclohexyl, or trihalomethylthio (as SCCl3).

The compounds of the present invention may be prepared by reacting a haloalkylsulfenyl halide with an alkali metal salt of a 2,4-dioxo or 2-thiono-4-oxo-1,3-dihydroquinazoline as described in U.S. Pat. No. 4,551,458.

The haloalkylthio 2,4-dioxo- or 2-thiono-4-oxo 1,3-dihydroquinazolines of the present invention can be formulated as herbicides. They can be compounded as standard formulations such as solutions, emulsions, suspensions, powders, pastes and granulates. Those may be produced in known manner, for example by mixing the active compounds with extenders, that is, liquid or solid diluents or carriers, optionally with the use of surface-active agents, that is, emulsifying agents and/or dispersing agents.

As liquid diluents or carriers, there can be used aromatic hydrocarbons, such as xylene or benzene; chlorinated aromatic hydrocarbons such as chlorobenzene; paraffins, such as mineral oil fractions; alcohols such as methanol or butanol; or strongly polar solvents such as dimethylformamide or dimethyl sulphoxide, as well as water.

As solid diluents or carriers, there can be used ground natural minerals, such as kaolins, clays, talc or chalk, or ground synthetic minerals, such as highly-dispersed silicic acid or silicates.

Examples of emulsifying agents include non-ionic and anionic emulsifiers, such as polyoxyethylene-fatty acid esters, polyoxyethylene-fatty alochol ethers, for example alkylarylpolyglycol ethers, alkyl sulphonates and aryl sulphonates, examples of dispersing agents, include lignin, sulphite waste liquors, and methylcellulose.

The active compounds according to the invention may be present in the formulations in admixture with other active compounds, such as fungicides, insecticides of other herbicides.

The formulations contain, in general, from 0.01 to 95, preferably 0.1 to 90 percent by weight of active compound; and the active compounds are applied at a rate of from 0.10 to 1.7 kg per hectare.

The active compounds may be used as such or in the form of their formulations prepared therefrom, such as ready-to-use solutions, emulsifiable concentrates, emulsions, suspensions, spray powders, pastes, soluble powders, dusting agents and granulates. Application may take place in the usual manner, for example by watering, squirting, atomizing, vaporization, fumigation, scattering or dusting.

The invention, therefore, provides herbicidal compositions containing as active ingredient a compound according to the invention in admixture with a solid or liquid diluent or carrier.

The invention also provides a method of combating unwanted vegetation which comprises applying to the vegetation either to the seeds prior to germination or directly to the plants in the seedling stage a composition containing as active ingredient a compound according to the invention in admixture with a solid or liquid diluent or carrier.

EXAMPLE 1

Preparation of 1-trichloromethylthio-3-cyclohexyl-2,4-dioxo-1,3-dihydroquinazoline To a suspension of 12.2gr (0.05 mole) 3-cyclohexyl-2,4-dioxo-1,3-dihydroquinazoline in 200 ml water and 50 ml methyl ethyl ketone (MEK) was added a solution of 0.05 mole potassium hydroxide in 6.4 ml water. To this basic solution (pH: 13.3) was added dropwise, during 5 minutes a mixture of 0.05 mole trichloromethyl sulfenyl chloride and 0.12gr emulsifier (ethylated castor oil) dissolved in 1 ml MEK while maintaining the reaction mixture at 2°-5° C.

The pH of the reaction mixture was kept constant by adding a 30% solution of potassium hydroxide. After mixing for 20 minutes the precipitate formed was filtered off and the filter cake was washed with water and air-dried. This afforded 12.5gr of crude material. The crude material was extracted with toluene and further purified to afford 5.5gr (28% yield) pure 1-trichloromethylthio-3-cyclohexyl-2,4-dioxo-1,3 dihydroquinazoline having a melting point of 139°-140° C. NMR and MS spectrographic methods confirms the structure. The unreacted starting material can be used again, improving the overall yield of the reaction.

EXAMPLE 2–12

Post-Emergence Herbicidal Activity

The test of post-emergence herbicidal activity is based on spraying young plants (5 cm high) of oats (*Avena Sativa*, Var. "Fulgum"), red beet (*Beta vulgaris*, Var. "Egypian"), cucumber (*Cucunnis sativus*, Var. "Delila"), lettuce (*Lactuca sativa*, Var. "Naga 936"), and tomato (*Lycopersicum esculentum;* Var, VF-134-1). The plants are kept in small plastic beakers containing inert sand, (diamater of 4.5 cm), one plant in each beaker. The compounds of the present invention are applied by area spraying of each beaker at a rate of application of from 0.10 to 1.7 kg active ingredient per hectare. For example 10 mg of active compound is dissolved in 1 ml DMF:acetone (2:1), 20 $\mu$l of TAPRI (a surface active agent, a product of Makhteshim Chemical Works Ltd.) and 9 ml of water. This rate of application is equivalent to 1.7 kg active ingredient per hectare. The progress was checked and recorded 3, 6, 10 and 14 days after spraying. The results are shown in Table 1.

EXAMPLE 13

The post-emergence activity of the compound used in Example 8 was tested at an application rate of 0.10 kg per hectare. Greater than 60% damage or total death was found against tomate, lettuce, and cucumber.

EXAMPLE 14–22

Pre-Emergence Herbicidal Activity

The test of pre-emergence herbicidal activity is based on spraying earth containing seeds of oat, tomato, lettuce, and cucumber (of the types described for Examples 2–12). The seeds are kept in a plastic beaker (diameter of 10 cm) containing inert sand 0.5 cm below the surface. The seeds are then sprayed using the mixture and rate of application described for Examples 2–12. Seven days after spraying from 0.5 cm to 2 cm of a plant emerges which after about 3 days dies. The results are shown in Table 2, with no activity shown against oats.

TABLE 1

| | | | | POST-EMERGENCE HERBICIDAL ACTIVITY[a] | | | | |
|---|---|---|---|---|---|---|---|---|
| | | | | | | Phytotoxicity Index[b] | | |
| Example | R | R' | R' | Oat A[c] | Tomato A B C D | Lettuce A B C D | Cucumber A B C D | Beet A B C D |
| 2 | H | 1-SCCl$_3$ | 3-SCCl$_3$ | 0 | 1 | 1 | 2 | 1 |
| 3 | H | 1-SCCl$_3$ | 3-n-propyl | 0 | 3 0 | 3 2 | 3 0 | 3 2 |
| 4 | H | 1-SCCl$_3$ | 3-iso-propyl | 0 | 3 3 | 3 3 | 3 3 | 3 3 |
| 5 | H | 1-SC$_2$Cl$_4$H | 0 | 3 3 | 3 3 | 3 3 | 3 3 | |
| 6 | H | 1-SC$_2$Cl$_4$H | 0 | 3 3 | 3 2 | 3 3 | 3 3 | |
| 7 | 6-CH$_3$ | 1-SCCl$_3$ | 3-iso-propyl | 0 | 3 3 0 | 3 3 0 | 3 3 3 | 3 3 0 |
| 8 | H | 1-SCCl$_3$ | 3-cyclohexyl | 0 | 3 3 3 | 3 3 3 | 3 3 3 | 3 3 3 |
| 9 | H | 1-SCCl$_3$ | 3-n-butyl | 0 | 3 0 | 3 3 | 3 2 | 3 3 |
| 10 | 6-CH$_3$ | 1-SCCl$_3$ | 3-cyclohexyl | 0 | 3 3 0 0 | 3 3 2 2 | 3 3 3 3 | 3 3 3 3 |
| 11 | 6-CH$_3$ | 1-SCCl$_3$ | 3-n-butyl | 0 | 0 0 | 0 0 | 2 0 | 1 0 |
| 12 | H | 1-SCCl$_3$ | 3-isobutyl | 0 | 3 0 | 3 1 | 3 3 | 3 1 |

[a]Evaluated 14 days after foliar spray of seedling 5–7 cm in height
[b]Index of Phytotoxicity: 0 - no phytotoxicity 1 - 10 to 30% of leaf areas damaged 2 - 30 to 60% of leaf areas damaged 3 - Greater than 60% damage or total death
[c]Key to rate of application: A: 1.7 kg/hectare B: 0.85 kg/hectare C: 0.43 kg/hectare D: 0.22 kg/hectare

TABLE 2

| | | | | PRE-EMERGENCE HERBICIDAL ACTIVITY | | | |
|---|---|---|---|---|---|---|---|
| | | | | Results[a] | | | |
| Example | R | R' | R' | Oat | Tomato | Lettuce | Cucumber |
| 14 | 6-CH$_3$ | 1-SCCl$_3$ | 3-iso-propyl | Inactive | Active | Active | Active |
| 15 | H | 1-SCCl$_3$ | 3-cyclohexyl | Inactive | Active | Active | Active |
| | | | | | Inactive[b] | Active[b] | Active[b] |
| 16 | H | 1-SCCl$_3$ | 3-n-butyl | Inactive | Active | Active | Active |
| 17 | H | 1-SCCl$_3$ | 3-iso-propyl | Inactive | Active | Active | Active |
| 18 | H | 1-SC$_2$Cl$_4$H | 3-iso-propyl | Inactive | Active | Active | Active |
| 19 | H | 1-SC$_2$Cl$_4$H | 3-n-propyl | Inactive | Inactive | Active | Inactive |
| 20 | H | 1-SCCl$_3$ | 3-n-propyl | Inactive | Active | Active | Active |
| 21 | H | 1-SCCl$_3$ | 3-isobutyl | Inactive | Inactive | Active | Active |
| 22 | 6-CH$_3$ | 1-SCCl$_3$ | 3-cyclohexyl | Inactive | Inactive | Active | Active |
| | | | | | Inactive[c] | Active[c] | Active[c] |
| | | | | | Inactive[b] | Inactive[b] | Active[b] |

[a]Key: Active - total death 3 days after emergence and 10 days aftar spraying
Inactive - not affected
[a]Application rate of 1.7 kg per hectare except where noted
[b]Application rate of 0.43 kg per hectare
[c]Application rate of 0.85 kg per hectare

We claim:

1. A method of controlling broadleaved weeds in cereal crops, comprising applying to a field of a cereal crop, pre-emergently or post-emergently, a composition comprising an agricultural carrier and an herbicidally effective amount of an active compound of the formula:

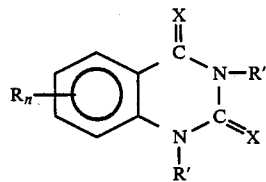

wherein
R is hydrogen, lower alkyl, lower alkoxy, amino, substituted amino, cycloalkyl, halogen, or nitro;
R' is selected from the group consisting of a haloalkylthio group containing 1 or 2 carbon atoms and at least two halogen substituents; linear or branched alkyl and alkenyl group having from 2 to 10 carbon atoms, optionally substituted by halogen, hydroxy, lower alkoxy, or haloalkyl; and cycloalkyl of 5 to 10 carbon atoms, optionally substituted by halogen, hydroxy, lower alkoxy, or haloalkyl; provided that at least one of R' is a haloalkylthio group as defined;
n is zero or an integer from 1 to 4; and
X is oxygen or sulfur.

2. A method in accordance with claim 1 wherein said cereal crop is oats.

3. A method in accordance with claim 1 wherein the active compound is applied at a rate of from 0.10 to 1.7 kg per hectare.

4. A method of controlling broadleaved weeds which comprises applying to the broadleaved weeds a herbicidally effective amount of a compound of the formula:

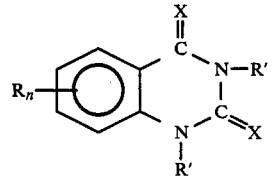

wherein
R is hydrogen, lower alkyl, lower alkoxy, amino, substituted amino, cycloalkyl, halogen, or nitro;
R' is selected from the group consisting of a haloalkylthio group containing 1 or 2 carbon atoms and at least two halogen substituents; linear or branched alkyl and alkenyl group having from 2 to 10 carbon atoms, optionally substituted by halogen, hydroxy, lower alkoxy, or haloalkyl; and cycloalkyl of 5 to 10 carbon atoms, optionally substituted by halogen, hydroxy, lower alkoxy, or haloalkyl; provided that at least one of R' is a haloalkylthio group as defined;
n is zero or an integer from 1 to 4; and
X is oxygen or sulfur.

5. A method in accordance with claim 4 wherein said at least one R' which is haloalkylthio is a trichloromethylthio group.

6. A method in accordance with claim 4 wherein X is oxygen.

7. A method in accordance with claim 4 wherein R is hydrogen or lower alkyl; n is 1; and one R' is a trichloromethylthio group or an alkyl group having at least three carbon atoms.

8. A method in accordance with claim 4 wherein one R' is selected from the group consisting of n-propyl, isopropyl, n-butyl and cyclohexyl.

* * * * *